US00PP19005P2

(12) United States Plant Patent
Higaki

(10) Patent No.: US PP19,005 P2
(45) Date of Patent: Jul. 8, 2008

(54) ***HYDRANGEA* PLANT NAMED 'FANTASY'**

(50) Latin Name: *Hydrangea macrophylla*
Varietal Denomination: Fantasy

(75) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 11/707,508

(22) Filed: Feb. 15, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
(74) *Attorney, Agent, or Firm*—James R. Cypher; Charles R. Cypher

(57) ABSTRACT

A new and distinct cultivar of *Hydrangea macrophylla* (Thunb.) named 'Fantasy' originated as a controlled cross. The cultivar 'Fantasy' can be blue or pink depending on the acidity of the soil and is desirable for its compact and sturdy growth habit. 'Fantasy' has large showy inflorescences, having both sepalous and non-sepalous florets.

4 Drawing Sheets

Botanical classification: *Hydrangea macrophylla* (Thunb.) 'Fantasy'.
Variety denomination: 'Fantasy'.

BACKGROUND OF THE INVENTION

This invention relates to a new and distinct cultivar of the Saxifragaceae family. The botanical name of the plant is *Hydrangea macrophylla* (Thunb.) 'Fantasy'.

The new cultivar originated as a seedling from a controlled cross.

The variety 'Fantasy' has lightly pigmented sepals. The new variety was first noticed, because it combined the desirable growth characteristics of its parents while producing flowers with lightly pigmented sepals.

The new cultivar 'Fantasy' has been successfully asexually reproduced under controlled environmental conditions at a nursery in Half Moon Bay, Calif. under the direction of the inventor over a three year period with its distinguishing characteristics remaining stable.

Asexual reproduction was first accomplished when vegetative cuttings were taken from the initially selected plant. Examination of asexually reproduced, successive generations grown in at Half Moon Bay, Calif. show that the combination of characteristics as herein disclosed for 'Fantasy' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
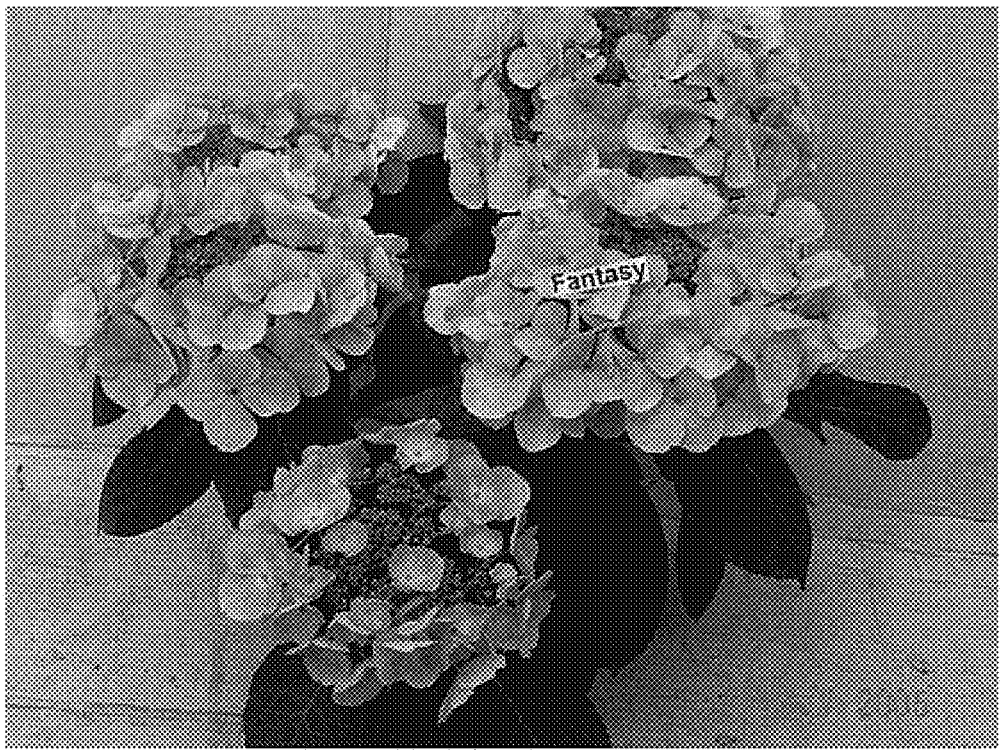
FIG. 1 is a view of the entire plant showing its form, compact growth habit, dark green foliage, inflorescence, and pink sepals.
Figure 2:
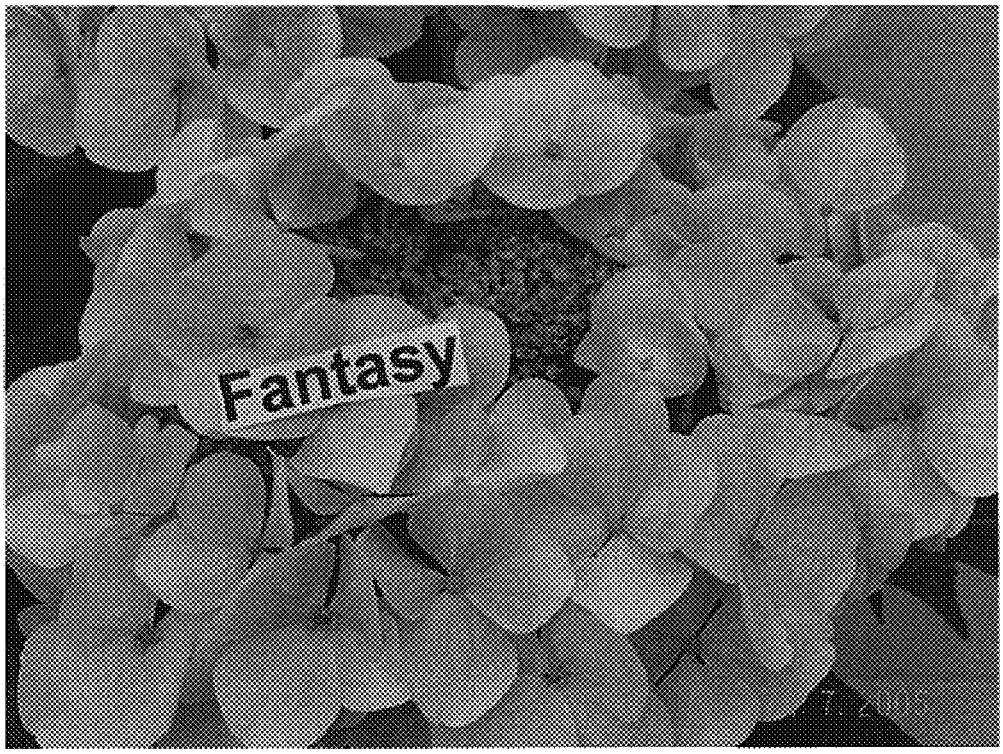
FIG. 2 is a close-up view of a panicle of the new variety, showing opened, sepalous florets and non-sepalous florets.
Figure 3:
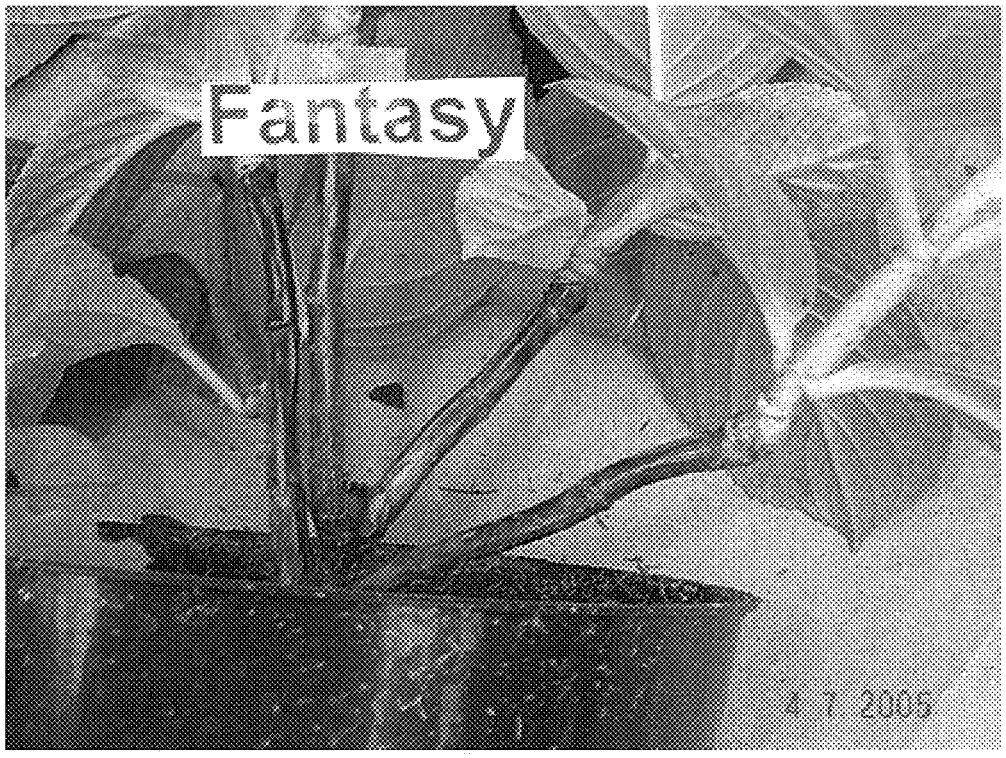
FIG. 3 is a close-up view of the base of the stem.
Figure 4:
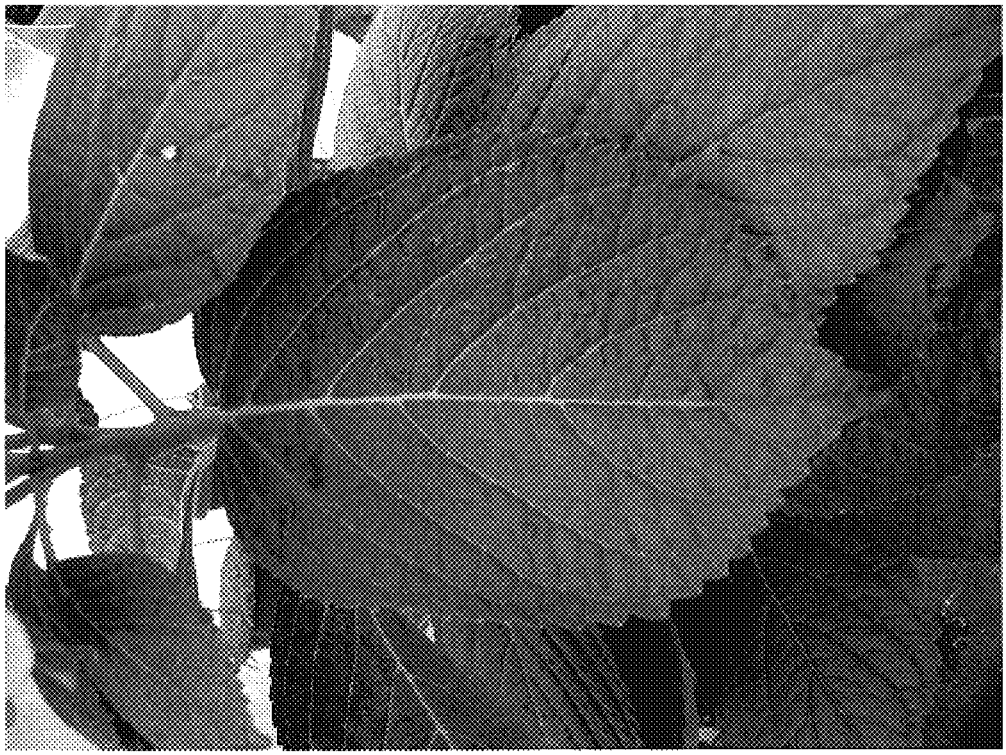
FIG. 4 is a close-up view of the adaxial surface of a mature leaf.
Figure 5:
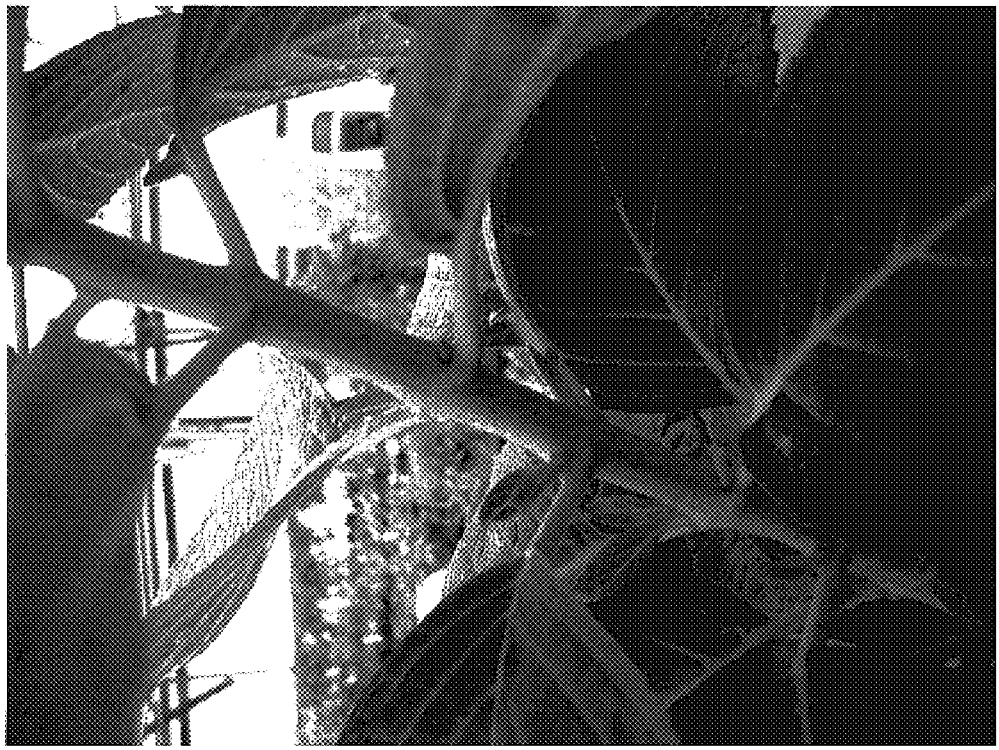
FIG. 5 is a close-up view of a non-woody portion of the stem, showing lenticels on the stem.
Figure 6:
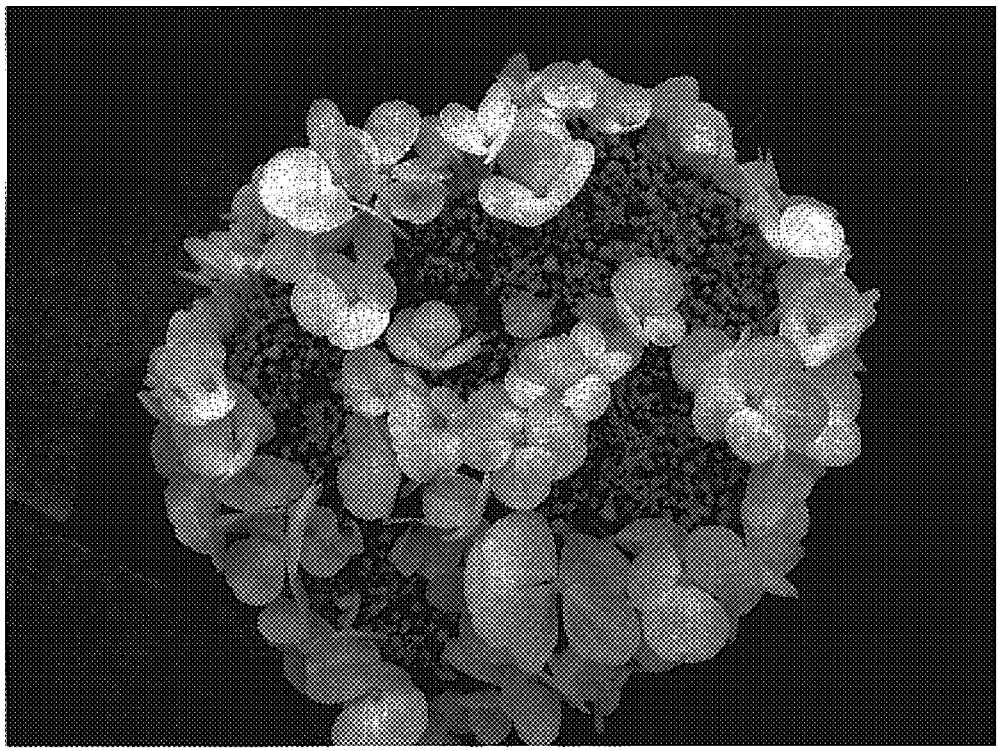
FIG. 6 is a close-up view of a panicle of the new variety. The panicle shown is still rather young. The sepalous florets are newly opened, and the pigmentation of the sepals is still light.
Figure 7:
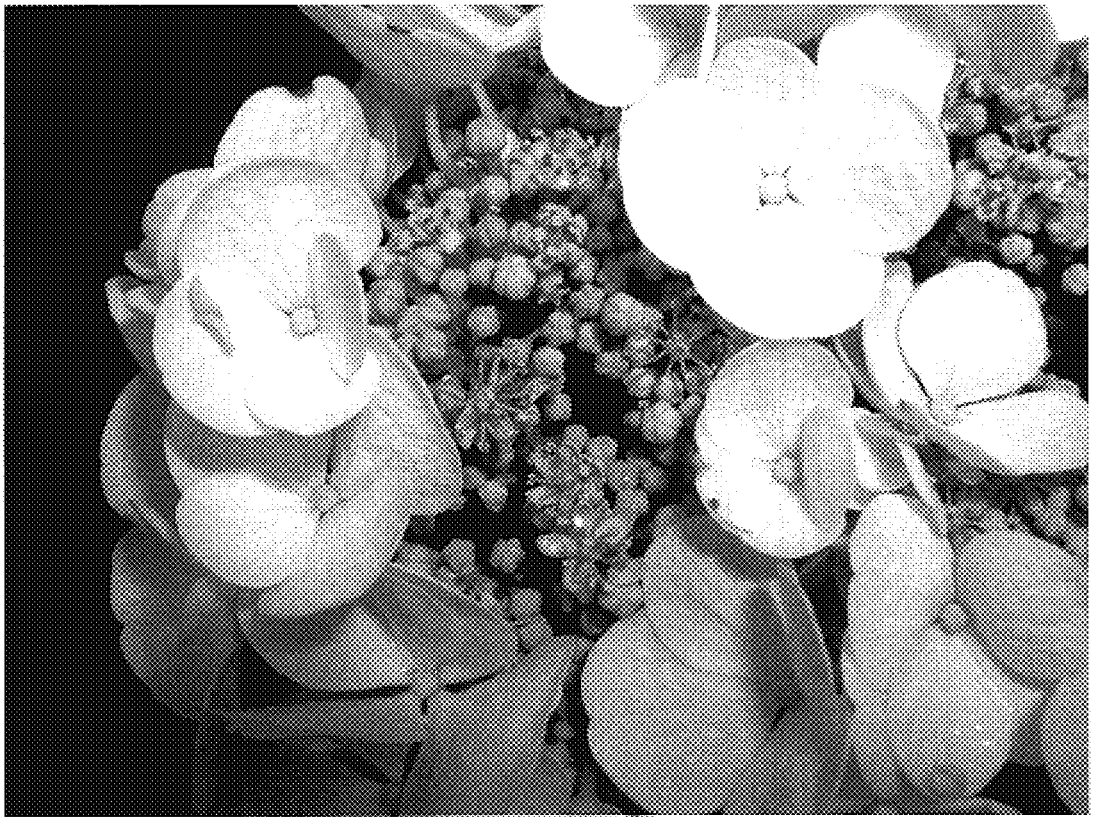
FIG. 7 is a close-up view of a panicle of the new variety. The panicle shown is still rather young. The sepalous florets are newly opened, and the pigmentation of the sepals is still light.

The plants shown in the figures are approximately 1 years old. The plant started out as cuttings, taken from the stem of a grown plant.

'Fantasy' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross.

Form: Upright, compact shrub. A typical plant with a mature inflorescence that is ready for sale is approximately 17" high and has a diameter of 16" when grown in a 4" pot with appropriate soil amendments.

Growth: Upright, vigorous growth habit. Inflorescence is large. The plant branches easily with shoots forming at the base of the plant. Lateral branches are similar in appearance and form to the main stems.

Stems: Lenticels are present. Stems become woody as they age. The color of typical young stems and young lateral branches is R.H.S. 145 A (green group).

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the leaf surface.

*Color.*—Mature leaves have an upper side that is R.H.S. 147 A (yellow — green group), and an under side that is R.H.S. 138 B (green group). Leaves are pinnately veined. The midvein and veins branching off the midvein are large and prominent on the underside of the leaves. Leaves are as wide as 5" and 7.7" long. Petioles are typically 1" long.

BUDS

Form: Globose with 4 to 5 connate petals. Buds in the center of the inflorescence are non-sepalous. The majority of buds do not the sepals. They are approximately 1 mm by 1 mm when very young. Buds can be 5 mm in diameter and still unopened.

Aspect: Smooth.

Arrangement: Borne on branched panicles.

INFLORESCENCE

Form: Paniculate. Terminal. As many as 100 or more individual flowers (florets) per inflorescence. Both sepalous florets and non-sepalous florets borne on same panicle. Flowers do not produce a fragrance. The peduncle or panicle for the inflorescence is strong and upright.

Size of Inflorescence: Large. Individual inflorescence size is dependent on the number of florets. A typical inflorescence can grow as large as 9" in diameter, and 5.5" high.

Shape: Clusters of numerous small florets; sepalous florets are flat and overlapping one another. Sepals are persistent.

Appearance: Showy.

FLORETS

General: The non-sepalous florets at the center of the inflorescence open first. Sepalous florets are perfect and complete.

Corolla: Generally there are 5 petals which fall off as flower matures. Petals are typically 4 mm long and 3 mm wide.

Stamens.—10 stamens. Pollen is white — R.H.S. 158C (yellow-white group). Plants produces abundant pollen. Filament is approximately 2 mm long. Anther is 1 mm long and is regular and basally attached.

Stigma: Two to three style each, although most florets have two style. Each style has one stigma. Style is typically 2 mm long.

Ovary: Ovary is partially inferior.

Sepalous florets:

*General.*—Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges often wavy when the floret is young.

*Size of sepals.*—As the florets mature, the sepals enlarge and overlap each other more and more, until, often, there is no space between the sepals when the petals of the florets open. Sepals at maturity are typically 2.5 cm long and 2 cm wide. Flowers are typically 4.5 cm in diameter.

Fruit: None.

I claim:

1. A new and distinct *Hydrangea macrophylla* plant named 'Fantasy' substantially as herein shown and described.

* * * * *